(12) United States Patent
Metzger et al.

(10) Patent No.: US 8,206,452 B2
(45) Date of Patent: Jun. 26, 2012

(54) PROSTHETIC DEVICE WITH DAMPER

(75) Inventors: Robert Metzger, Wakarusa, IN (US); Brian A. Uthgenannt, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 47 days.

(21) Appl. No.: 12/708,247

(22) Filed: Feb. 18, 2010

(65) Prior Publication Data
US 2011/0202139 A1    Aug. 18, 2011

(51) Int. Cl.
*A61F 2/38* (2006.01)
(52) U.S. Cl. .................................................. 623/20.27
(58) Field of Classification Search .... 623/20.14–20.33, 623/23.17, 23.15, 22.42, 22.45, 22.46
See application file for complete search history.

(56) References Cited

U.S. PATENT DOCUMENTS

| | | | | |
|---|---|---|---|---|
| 4,129,903 A * | 12/1978 | Huggler | ...................... | 623/23.11 |
| 4,538,305 A * | 9/1985 | Engelbrecht et al. | ...... | 623/20.25 |
| 4,950,297 A | 8/1990 | Elloy et al. | | |
| 5,201,881 A | 4/1993 | Evans | | |
| 5,330,534 A | 7/1994 | Herrington et al. | | |
| 5,344,459 A * | 9/1994 | Swartz | ...................... | 623/14.12 |
| 5,358,525 A * | 10/1994 | Fox et al. | .................... | 623/14.12 |
| 5,389,107 A * | 2/1995 | Nassar et al. | .............. | 623/23.17 |
| 5,906,643 A | 5/1999 | Walker | | |
| 6,099,570 A * | 8/2000 | Livet et al. | ................. | 623/20.21 |
| 6,217,619 B1 * | 4/2001 | Keller | ......................... | 623/20.34 |
| 6,336,941 B1 * | 1/2002 | Subba Rao et al. | ........ | 623/22.42 |
| 6,413,279 B1 * | 7/2002 | Metzger et al. | ............ | 623/20.29 |
| 6,629,999 B1 * | 10/2003 | Serafin, Jr. | ................. | 623/20.15 |
| 6,875,235 B2 * | 4/2005 | Ferree | ......................... | 623/20.32 |
| 6,972,039 B2 * | 12/2005 | Metzger et al. | ............ | 623/20.29 |
| 6,986,791 B1 * | 1/2006 | Metzger | ..................... | 623/20.24 |
| 7,175,666 B2 * | 2/2007 | Yao | ............................. | 623/20.33 |
| 7,179,295 B2 * | 2/2007 | Kovacevic | .................. | 623/17.15 |
| 7,235,102 B2 * | 6/2007 | Ferree et al. | ............... | 623/17.12 |
| 7,244,274 B2 | 7/2007 | Delfosse et al. | | |
| 7,288,115 B2 * | 10/2007 | Hawkins | ..................... | 623/20.14 |
| 7,381,223 B2 * | 6/2008 | Kovacevic | .................. | 623/20.32 |
| 7,572,292 B2 * | 8/2009 | Crabtree et al. | ........... | 623/20.24 |
| 7,597,713 B2 * | 10/2009 | Baumgartner et al. | .... | 623/17.15 |
| 7,658,767 B2 * | 2/2010 | Wyss | ......................... | 623/20.29 |
| 7,803,193 B2 * | 9/2010 | Steinberg | .................... | 623/20.21 |
| 7,871,442 B2 * | 1/2011 | Servidio | ..................... | 623/20.27 |
| 7,918,893 B2 * | 4/2011 | Romeis et al. | ............. | 623/20.24 |
| 2004/0024460 A1 * | 2/2004 | Ferree | ......................... | 623/17.12 |
| 2006/0064169 A1 * | 3/2006 | Ferree | ......................... | 623/17.12 |
| 2007/0135926 A1 * | 6/2007 | Walker | ........................ | 623/20.31 |
| 2008/0097616 A1 * | 4/2008 | Meyers et al. | ............. | 623/20.29 |
| 2008/0275559 A1 * | 11/2008 | Makower et al. | .......... | 623/20.14 |
| 2008/0275560 A1 * | 11/2008 | Clifford et al. | ............. | 623/20.15 |
| 2008/0275565 A1 * | 11/2008 | Makower et al. | .......... | 623/20.22 |
| 2009/0125108 A1 * | 5/2009 | Linares | ...................... | 623/14.12 |
| 2010/0114322 A1 * | 5/2010 | Clifford et al. | ............. | 623/20.14 |
| 2011/0040387 A1 * | 2/2011 | Ries et al. | .................. | 623/20.27 |
| 2011/0066248 A1 * | 3/2011 | Ries et al. | .................. | 623/20.32 |

* cited by examiner

*Primary Examiner* — Alvin J Stewart
(74) *Attorney, Agent, or Firm* — Harness, Dickey

(57) ABSTRACT

A prosthetic joint assembly supports articulation of a joint. The joint assembly includes a first component configured to be fixed to an anatomical feature. The first component includes a first impact surface and a second component that engages the first component. The second component includes a second impact surface that impacts the first impact surface as the first component moves relative to the second component. Furthermore, at least one of the first impact surface and the second impact surface includes a dampening member that dampens energy resulting from impact of the first and second impact surfaces.

12 Claims, 2 Drawing Sheets

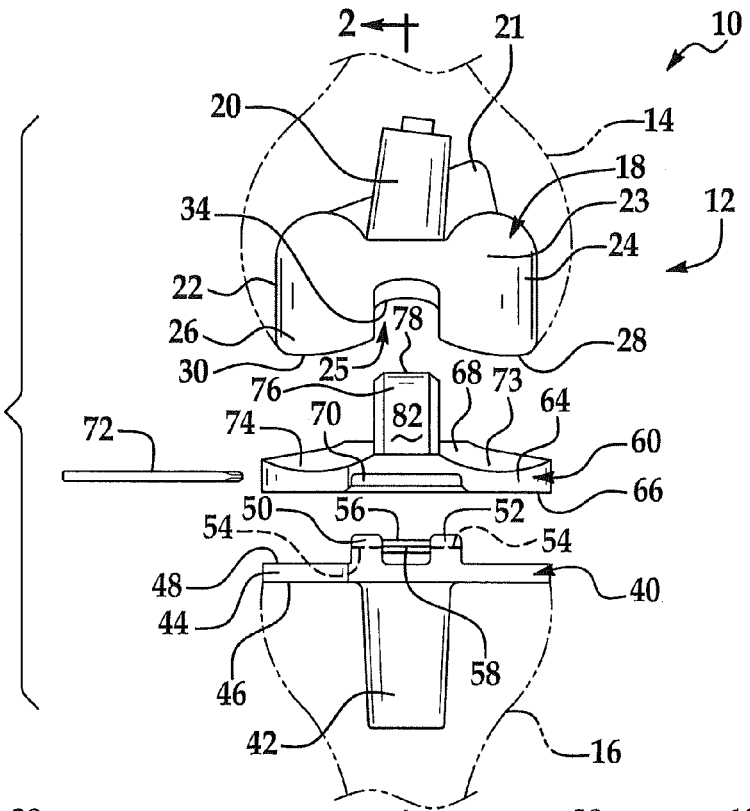
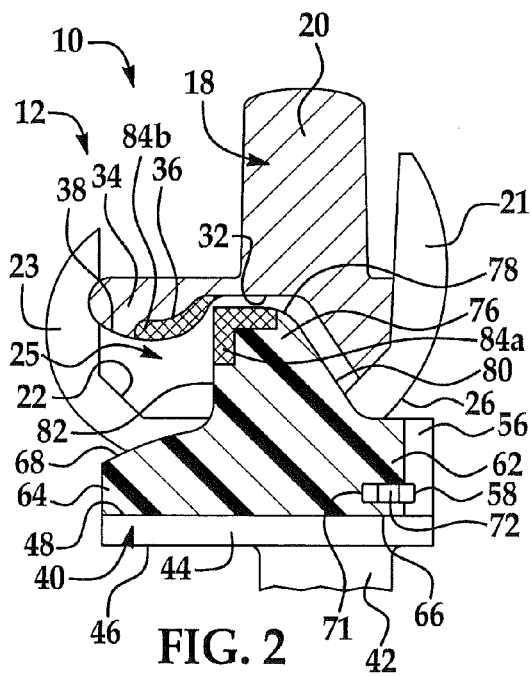
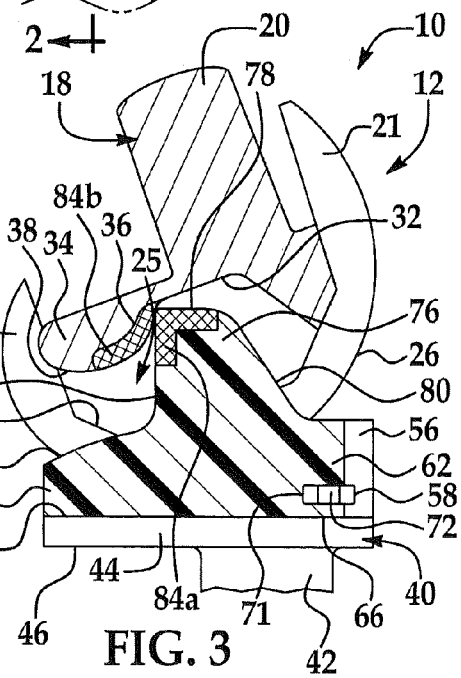
FIG. 1
FIG. 2
FIG. 3

PROSTHETIC DEVICE WITH DAMPER

FIELD

The following relates to a prosthetic device and, more particularly, to a prosthetic device with a damper.

BACKGROUND

The statements in this section merely provide background information related to the present disclosure and may not constitute prior art.

Prosthetic joints can reduce pain due to arthritis, deterioration, deformation, and the like, and can improve mobility of the joint. Oftentimes, prosthetic joints can include certain implantable prosthetic members that are fixed to the patient's anatomy. For instance, knee joint prosthetic devices can include a femoral component fixed to the patient's femur and a tibial component fixed to the patient's tibia. Also, the device can include a bearing disposed between the femoral and tibial components. The bearing can be supported by the tibial component, and the bearing can include a bearing surface. An articulating surface of the femoral component can articulate on the bearing surface of the bearing.

In some cases, these components can include surfaces that impact each other during articulation of the joint. For instance, in some embodiments, surfaces of the femoral component can impact surfaces of the bearing when the femoral component moves relative to the bearing. Also, in some embodiments, surfaces of the bearing can impact surfaces of the tibial component when the bearing moves relative to the tibial component.

SUMMARY

A prosthetic joint assembly is disclosed that supports articulation of a joint. The joint assembly includes a first component configured to be fixed to an anatomical feature. The first component includes a first impact surface and a second component that engages the first component. The second component includes a second impact surface that impacts the first impact surface as the first component moves relative to the second component. Furthermore, at least one of the first impact surface and the second impact surface includes a dampening member that dampens energy resulting from impact of the first and second impact surfaces.

A method of implanting a prosthetic joint assembly into a patient is also disclosed. The method includes fixing a first component of the prosthetic joint assembly to an anatomical feature. The first component includes a first impact surface. Moreover, the method includes supporting a second component of the prosthetic knee assembly for movement relative to the first component such that a second impact surface of the second component impacts the first impact surface of the first component as the second component moves relative to the first component. At least one of the first impact surface and the second impact surface includes a dampening member that dampens energy resulting from impact of the first and second impact surfaces.

Moreover, a prosthetic knee assembly for supporting articulation of a knee joint is disclosed. The knee assembly includes a femoral component having an articulating surface and a tibial component having a tray and a projection that extends in a superior direction from the tray. The bearing is moveably supported on the tray, and the bearing includes a bearing surface that supports the articulating surface for articulation thereon. The bearing also includes an aperture with an inner surface, and the aperture receives the projection of the tibial component for movement therein. At least one of the projection and the inner surface of the aperture includes a hollow, tubular sound dampening member that dampens noise resulting from impact of the bearing and the tibial component.

Still further, a prosthetic knee assembly for supporting articulation of a knee joint is disclosed. The knee assembly includes a tibial component and a femoral component having an articulating surface and a cam. The cam includes a cam surface. Furthermore, the knee assembly includes a bearing fixed to the tray. The bearing includes a bearing surface that supports the articulating surface for articulation thereon. The bearing also includes a projection that extends in a superior direction away from the bearing surface. The cam cams against the projection to cam the femoral component relative to the bearing. Moreover, at least one of the cam surface and the projection surface includes a sound dampening member that dampens noise resulting from impact of the bearing and the femoral component.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 is an exploded, posterior view of a prosthetic joint assembly according to various exemplary embodiments of the present disclosure;

FIG. 2 is a sectional view of the prosthetic joint assembly in an assembled state that is taken along the line 2-2 of FIG. 1;

FIGS. 3 and 4 are sectional views of the prosthetic joint assembly of FIG. 2, each shown in different stages of articulation;

DETAILED DESCRIPTION

Figure 4:
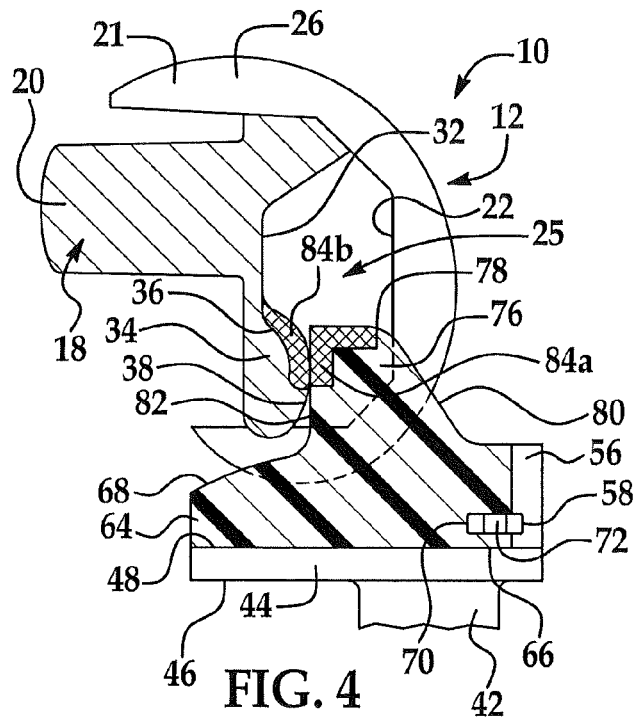

The following description is merely exemplary in nature and is not intended to limit the present disclosure, application, or uses. It should be understood that throughout the drawings, corresponding reference numerals indicate like or corresponding parts and features.

Referring initially to FIG. 1, a prosthetic joint assembly 10 is illustrated according to various exemplary embodiments of the present disclosure. The assembly 10 can be a knee joint assembly 12 for supporting articulation of a knee joint; however, the assembly 10 can be for any joint other than a knee joint without departing from the scope of the present disclosure.

As shown, the knee joint assembly 12 can be secured to a femur 14 and a tibia 16 of a surgically resected left knee joint (the femur 14 and the tibia 16 shown in phantom). It will be understood that while the knee joint assembly 12 can be implanted into a left knee joint, the knee joint assembly 12 can be configured for implantation into a right knee joint. It will also be appreciated that the knee joint assembly 12 can be configured as a cruciate retaining (CR) joint assembly, a posterior stabilized (PS) joint assembly, a fully constrained joint assembly, a hinged knee joint assembly, or any other suitable knee joint assembly 12.

Specifically, the knee joint assembly 12 can include a femoral component 18 that can be secured to the distal end of the femur 14 after the femur 14 has been resected in a manner well known in the art. The femoral component 18 can be fixed to the femur 14 via fasteners, bone cement, and/or any other suitable means. Also, the femoral component 18 can be unitary and monolithic in structure and can be made from any suitable biocompatible material.

The femoral component 18 can include a stem 20, which can be tubular in shape and can be received and fixed in a bore (not specifically shown) formed in the resected femur 14. The femoral component 18 can also include a patellar track 21, a posterior portion 23, and a plurality of condyles 24, 26, which are spaced apart in the medial-lateral direction to define an intercondylar box 25. Moreover, the femoral component 18 can include a bone engaging surface 22 (FIGS. 2-4).

The bone engaging surface 22 (FIGS. 2-4) can include one or more planar and/or curved surfaces that engage and fit to corresponding surfaces of the resected femur 14. The condyles 24, 26 can be opposite the bone engaging surface 22 and can include a first condyle 24 and a second condyle 26. The first and second condyles 24, 26 can have a shape substantially similar to anatomical condyles of a femur 14. The first condyle 24 can include a first articulating surface 28, and the second condyle 26 can include a second articulating surface 30 (FIG. 1). The first and second articulating surfaces 28, 30 can be polished so as to provide a substantially smooth surface for supporting articulation of the knee joint assembly 12.

The intercondylar box 25 can define an intercondylar recess 32 and a cam 34 (FIGS. 2-4). The cam 34 can be disposed in a posterior direction relative to the recess 32. The cam 34 can be bulbous and continuous in shape so as to include an anterior surface 36 (FIGS. 2-4) that faces the recess 32 and an inferior surface 38 (FIGS. 2-4). As will be discussed in greater detail below, the cam 34 can provide guided, camming movement of the femoral component 18 relative to other portions of the knee joint assembly 12.

Furthermore, the knee joint assembly 12 can include a tibial component 40 that can be fixed to a superior end of the resected tibia 16. The tibial component 40 can be fixed to the tibia 16 via fasteners, bone cement, and/or any other suitable means. The tibial component 40 can be unitary and monolithic and can be made of any suitable biocompatible material.

Generally, the tibial component 40 can include a stem 42 and tray 44. The stem 42 can be tubular and can be received and fixed in a bore (not specifically shown) formed in the resected tibia 16. The tray 44 can be substantially flat and can include a bone engaging surface 46 that engages the superior end of the resected tibia 16 and a superior surface 48 that is opposite the bone engaging surface 46. The bone engaging surface 46 can be porous, coated, or otherwise surface treated in a manner that promotes bone growth and attachment to the bone engaging surface 46. The tibial component 40 can further include a pair of integrally formed posts 50, 52 (FIG. 1), which extend superiorly from a posterior edge of the tray 44 (FIGS. 2-3). The posts 50, 52 can be spaced apart equally from a center of the tray 44. The posts 50, 52 can each include a posterior flange 54 (shown in phantom in FIG. 1). The tray 44 can also include an anterior projection 56 (FIG. 1) that extends superiorly from the anterior portion of the tray 44. The anterior projection 56 can include a channel 58.

Additionally, the knee joint assembly 12 can include a bearing 60. The bearing 60 can be a unitary, monolithic material made out of any suitable biocompatible material, such as polyethylene (e.g., ultra-high molecular weight polyethylene (UHMWPE), cross linked polyethylene, vitamin-E infused polyethylene, etc.) As shown in FIGS. 2-4, the bearing 60 can include an anterior portion 62, a posterior portion 64, an inferior surface 66, and a superior surface 68. As will be discussed in greater detail, the bearing 60 can engage both the femoral component 18 and the tibial component 40, and the bearing 60 can support articulation of the knee joint assembly 12.

The inferior surface 66 can be substantially flat and can be supported directly on the superior surface 48 of the tibial component 40. Moreover, the bearing 60 can include a posterior flange 70 (FIG. 1) and an anterior groove 71 (FIG. 2). A pin 72 can be received in the anterior groove 71 and the anterior groove 58 of the tibial component 40 (FIGS. 2 and 3) in order to fix the bearing 60 to the tibial component 40. Moreover, the posterior flange 70 can engage the posterior flange 54 of the tibial tray 44 (not specifically shown) in order to further secure the bearing 60 to the tibial component 40.

Moreover, the superior surface 68 of the bearing 60 can include a first bearing surface 73 and a second bearing surface 74 (FIG. 1), which can each have a three-dimensional concave curvature. The first bearing surface 73 can support the first articulating surface 28 for articulation thereon, and the second bearing surface 74 can support the second articulating surface 30 for articulation thereon. As such, the bearing surfaces 73, 74 can support articulation of the knee joint assembly 12 as the femoral component 18 moves relative to the bearing 60 and the tibial component 40.

In addition, the superior surface 68 of the bearing 60 can include a projection 76 (i.e., posterior-stabilizing post) that is disposed between and extends superiorly away from the first and second bearing surfaces 73, 74. As shown in FIGS. 1-4, the projection 76 can be substantially cubic in shape. As such, the projection 76 can include a superior surface 78, an anterior surface 80, and a posterior surface 82. The projection 76 can be sized and shaped so as to be received within the intercondylar recess 32 of the femoral component 18. Also, as will be discussed in greater detail, the cam 34 of the femoral component 18 can cam against the projection 76 to provide camming motion of the bearing 60 relative to the femoral component 18. During such movement, the cam 34 can impact the projection 76. More specifically, at certain positions of the femoral component 18 relative to the bearing 60 (e.g., FIG. 2), the cam 34 and projection 76 can be spaced apart, and during articulation of the joint (e.g., FIG. 3), the cam 34 and projection 76 can move toward each other to initially impact. Thus, the cam 34 and projection 76 can each define impacting surfaces as will be discussed in greater detail.

At least one of the impacting surfaces of the cam 34 and the projection 76 can include a dampening member 84a, 84b. For instance, the knee joint assembly 12 can include a first dampening member 84a and a second dampening member 84b (FIGS. 2-4). As will be discussed, the dampening members 84a, 84b can be disposed between the projection 76 of the bearing 60 and the cam 34 of the femoral component 18 to dampen energy that results when the femoral component 18 impacts the bearing 60. More specifically, the dampening members 84a, 84b can cushion the impact of the femoral component 18 and the bearing 60, and the dampening members 84a, 84b can dampen, reduce, and dissipate various forms of impact energy, such as audible noise, vibrations, shock impulse, kinetic energy, and the like, resulting from impact of the femoral component 18 and the bearing 60. For instance, sound that would otherwise occur if the femoral component 18 and the bearing 60 were to directly contact can be substantially reduced by the dampening members 84a, 84b. Accordingly, the knee joint assembly 12 can be less noticeable to the patient while the knee joint assembly 12 articulates.

For purposes of discussion, the dampening members 84a, 84b will be discussed primarily as reducing, damping, and dissipating impact sound, noise, and vibration. However, it will be appreciated that the dampening members 84a, 84b can reduce, dampen, and dissipate any other impact effects without departing from the scope of the present disclosure.

The dampening members 84a can be made out of a material having a lower stiffness and/or lower hardness than other portions of the bearing 60 (e.g., the bearing surfaces 73, 74). For instance, in some exemplary embodiments, the dampening member 84a can be made out of polyurethane (e.g., BIONATE polyurethane or other similar biocompatible polyurethane). Assuming the rest of the bearing 60 is made from polyethylene, the dampening member 84a can be an order of magnitude less stiff and approximately half as hard as the other portions of the bearing 60. The dampening member 84b can be made out of a material similar to the dampening member 84a.

The dampening members 84a, 84b can be disposed at any suitable location on the femoral component 18 and/or the bearing 60 where engagement or impact occurs (i.e., located on impacting surfaces of the femoral component 18 and/or the bearing 60). For instance, as shown in FIGS. 2-4, the first dampening member 84a can be disposed on and can define at least a portion of the superior surface 78 and the posterior surface 82 of the projection 76 of the bearing 60. Also, the second dampening member 84b can be disposed on and can define at least a portion of the anterior surface 36 and inferior surface 38 of the cam 34 of the femoral component 18. However, it will be appreciated that the dampening members 84a, 84b can be disposed between any surfaces of the bearing 60 and the femoral component 18 that would otherwise impact, abut, and/or make noise.

It will also be appreciated that the knee joint assembly 12 can include only one of the first and second dampening members 84a, 84b without departing from the scope of the present disclosure. As such, the knee joint assembly 12 can include only the first dampening member 84a. Also, the knee joint assembly 12 can include only the second dampening member 84b.

The first dampening member 84a can be fixed to the bearing 60 in any suitable fashion. The first dampening member 84a can be integrally coupled or removably coupled to the projection 76 of the bearing 60. For instance, the first dampening member 84a can be insert molded or otherwise molded to the projection 76, fixed by adhesives, fasteners, etc. The second dampening member 84b can be fixed to the cam 34 in a similar fashion.

Exemplary embodiments of articulation of the knee joint assembly 12 will now be discussed in greater detail. When in the position shown in FIG. 2, the articulating surfaces 28, 30 of the femoral component 18 can be slidingly supported on the bearing surfaces 73, 74 of the bearing 60. As the knee joint assembly 12 articulates, the articulating surfaces 28, 30 can continue to slide and articulate on the bearing surfaces 73, 74. Also, as the knee joint assembly 12 articulates away from the position of FIG. 2 and towards the positions of FIGS. 3 and 4, the cam 34 can cam against the projection 76. More specifically, the shape of the cam 34 causes the cam 34 to cammingly push against the projection 76 such that the bearing 60 and the tibial component 40 move in an anterior direction relative to the femoral component 18.

In addition, when the knee joint assembly 12 is in the position shown in FIG. 2, the cam 34 and the second dampening member 84b can be spaced apart from the projection 76 and the dampening member 84a. However, as the joint assembly 12 moves toward the position shown in FIG. 3, the second dampening member 84b can contact the first dampening member 84a and the cam 34 can impact the projection 76. Because of the relatively low stiffness and/or harness of the dampening members 84a, 84b, sound of such impact can be significantly reduced. Accordingly, articulation of the joint assembly 12 can be advantageously less noticeable, and potentially annoying clicking or popping noises are unlikely.

As stated above, the knee joint assembly 12 can include only one of the first and second dampening members 84a, 84b. For instance, when the knee joint assembly 12 includes the first dampening member 84a, the first dampening member 84a can directly contact the cam 34 during articulation of the knee joint assembly 12. Likewise, when the knee joint assembly 12 includes the second dampening member 84b, the second dampening member 84b can directly contact the projection 76. In either case, sounds caused by impact of these features can be significantly reduced.

Figure 5:
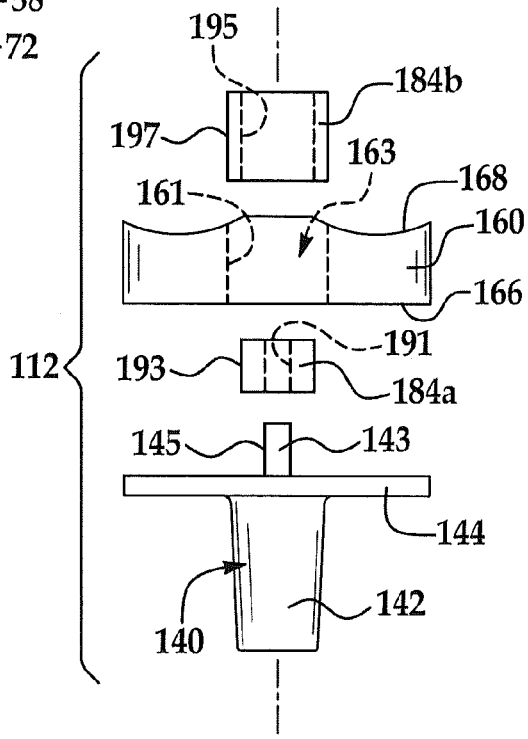
FIG. 5 is an exploded view of a prosthetic joint assembly according to further exemplary embodiments of the present disclosure.
Figure 6:
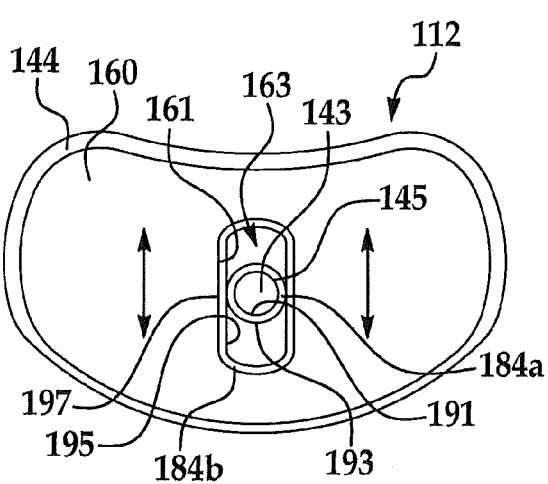
FIG. 6 is a top view of the prosthetic joint assembly of FIG. 5.

Referring now to FIGS. 5 and 6, further exemplary embodiments of the prosthetic knee joint assembly 112 are illustrated. Components that are similar to the embodiments of FIGS. 1-4 are indicated with similar reference numerals increased by 100.

As shown, the assembly 112 can include a tibial component 140 and a bearing 160. Although not shown, the assembly 112 can also include a femoral component of the type discussed above. As will be discussed, the bearing 160 can be supported for movement relative to the tibial component 140. This relative movement of the bearing 160 can allow for improved mobility of the assembly 112 as discussed in U.S. Pat. No. 6,972,039, filed Jul. 1, 2002, to Metzger et al., the disclosure of which is hereby incorporated by reference in its entirety.

The tibial component 140 can include a stem 142 and a tray 144. The tibial component 140 can also include a projection 143 that extends superiorly from the tray 144 on a side of the tray 144 opposite from the stem 142. The projection 143 can be tubular and can include an outer surface 145. Also, in some embodiments, the projection 143 (e.g., guide post) can be removably coupled to the tray 144 and/or stem 142 of the tibial component 140.

Moreover, the bearing 160 can include an aperture 163 (e.g., through hole) that extends between the inferior and superior surfaces 166, 168 of the bearing 160. As shown in FIG. 6, the aperture 163 can be a slot that extends in the anterior/posterior direction as represented by the vertical double headed arrows in FIG. 6. The projection 143 can be moveably received in the aperture 163 to allow the bearing 160 to move in the anterior/posterior direction relative to the tibial component 140. However, it will be appreciated that the aperture 163 can be of any suitable shape to allow any relative movement of the bearing 160 and tibial component 140. For instance, the aperture 163 can have a curved axis to allow rotation of the bearing 160 relative to the tibial component 140 about the projection 143. Furthermore, in some embodiments, the aperture 163 can have a shape that allows both linear movement and rotational movement of the bearing 160 relative to the tibial component 140.

The assembly 112 can also include a first dampening member 184a and a second dampening member 184b. The first and second dampening members 184a, 184b can each be ring-shaped (i.e., tubular and hollow). As such, the first dampening member 184a can include an inner surface 191 and an outer surface 193, and the second dampening member 184b can include an inner surface 195 and an outer surface 197. However, it will be appreciated that the first and second dampening members 184a, 184b can have any suitable shape.

Also, the first and second dampening members 184a, 184b can be disposed between the bearing 160 and the tibial component 140. For instance, the inner surface 191 of the first dampening member 184a can be fixed to the outer surface 145 of the projection 143, and the first dampening member 184a can enclose the projection 143. Also, the outer surface 197 of the second dampening member 184b can be fixed to the inner surface 161 of the bearing 160, and the bearing 160 can enclose the second dampening member 184b. In some embodiments, the first and second dampening members 184a, 184b can be molded, adhesively attached, or otherwise fixed to the projection 143 and the bearing 160, respectively. In other embodiments, the dampening members 184a, 184b can be removably coupled, such as via an interference fit, to the projection 143 and bearing 160, respectively.

As shown in FIG. 6, the projection 143 and the first dampening member 184a can be moveably received in the second dampening member 184b and the aperture 163. Accordingly, the bearing 160 can move relative to the tibial component 140, and the projection 143 can impact the bearing 160 to limit this relative motion. Also, the dampening members 184a, 184b can absorb the force and reduce the sound of such impact. Accordingly, the prosthetic knee joint assembly 112 is less noticeable during use.

Moreover, the knee joint assembly 112 can include only one of the first and second dampening members 184a, 184b. If only one of the dampening members 184a, 184b is included, sound of impact can be significantly reduced.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A prosthetic joint assembly supporting articulation of a joint comprising:
    a first component configured to be fixed to an anatomical feature, the first component including a first dampening member that defines a first impact surface; and
    a second component that engages the first component, the second component including a second dampening member that defines a second impact surface that impacts the first impact surface of the first dampening member as the first component moves relative to the second component;
    the first and second dampening members operable to dampen energy resulting from impact of the first and second impact surfaces,
    wherein the first component is a femoral component configured to be fixed to a femur, and wherein the second component is a bearing with a bearing surface, the femoral component including an articulating surface that is supported for articulation on the bearing surface of the bearing, the first dampening member having at least one of a lower stiffness and a lower hardness than the articulating surface, the second dampening member having at least one of a lower stiffness and a lower hardness than the bearing surface.

2. The prosthetic joint assembly of claim 1, wherein the first component includes a cam, the bearing also includes a projection, the cam cams against the projection to cam the first component relative to the bearing, the first dampening member at least partially defines the cam, and the second dampening member at least partially defines the projection.

3. The prosthetic joint assembly of claim 2, wherein the first dampening member only partially defines the cam, and wherein the second dampening member only partially defines the projection.

4. The prosthetic joint assembly of claim 3, wherein the projection includes an anterior face and a posterior face, the anterior and posterior faces are opposite each other, the second dampening member at least partially defines the posterior face.

5. The prosthetic joint assembly of claim 4, wherein the cam includes an anterior surface, and the first dampening member at least partially defines the anterior surface of the cam.

6. The prosthetic joint assembly of claim 1, wherein the bearing is supported for movement relative to the first component.

7. The prosthetic joint assembly of claim 6, wherein the second dampening member includes polyurethane and the bearing surface includes polyethylene.

8. The prosthetic joint assembly of claim 7, wherein the bearing surface includes at least one of ultra-high molecular weight polyethylene, cross linked polyethylene, and vitamin E infused polyethylene.

9. The prosthetic joint assembly of claim 1, wherein the first dampening member is integrally coupled to the first component so as to be monolithic and the second dampening member is integrally coupled to the second component so as to be monolithic.

10. A method of implanting a prosthetic joint assembly into a patient comprising:
    fixing a first component of the prosthetic joint assembly to an anatomical feature, the first component including a first dampening member that defines a first impact surface; and
    supporting a second component of the prosthetic assembly for movement relative to the first component, the second component including a second dampening member that defines a second impact surface that impacts the first impact surface of the first component as the second component moves relative to the first component, both of the first and second dampening members operable to dampen energy resulting from impact of the first and second impact surfaces, wherein the first component is a femoral component configured to be fixed to a femur, and wherein the second component is a bearing with a bearing surface, the femoral component including an articulating surface that is supported for articulation on the bearing surface of the bearing, the first dampening member having at least one of a lower stiffness and a lower hardness than the articulating surface, the second dampening member having at least one of a lower stiffness and a lower hardness than the bearing surface.

11. The method of claim 10, further comprising providing the first dampening member to at least partially define a cam of the femoral component and providing the second dampening member to at least partially define a projection of the bearing, the cam camming against the projection to cam the femoral component relative to the bearing.

12. The method of claim 10, wherein the first dampening member is integrally coupled to the femoral component so as to be monolithic and the second dampening member is integrally coupled to the bearing so as to be monolithic.

* * * * *